United States Patent [19]

Sandler et al.

[11] Patent Number: 5,576,344
[45] Date of Patent: Nov. 19, 1996

[54] PROCESS FOR REDUCING THE ADVERSE TASTE AND MALODOR ASSOCIATED WITH $H_2$-ANTAGONISTS

[75] Inventors: Patricia L. Sandler, Philadelphia, Pa.; Annabelle Mogavero, Marlton, N.J.; Kalpana Patel, Voorhees, N.J.; Alexander Seabrook, Sicklerville, N.J.

[73] Assignee: American Home Products Corporation, Madison, N.J.

[21] Appl. No.: 300,494

[22] Filed: Aug. 30, 1994

[51] Int. Cl.⁶ ............................................. A61K 9/08
[52] U.S. Cl. ................................ 514/427; 514/922
[58] Field of Search ............................ 424/467, 440, 424/484, 485; 514/819, 925, 922, 926, 421

[56] References Cited

U.S. PATENT DOCUMENTS

| | | | |
|---|---|---|---|
| 4,293,562 | 10/1981 | Ritter | 424/273 |
| 5,275,823 | 1/1994 | France | 424/489 |
| 5,380,535 | 1/1995 | Geyer et al. | 424/484 |

*Primary Examiner*—Thurman K. Page
*Assistant Examiner*—Sharon Howard
*Attorney, Agent, or Firm*—S. H. Flynn

[57] ABSTRACT

The present invention is directed to a process for reducing the adverse taste and malodor associated with the $H_2$-antagonist nizatidine. The process involves forming an aqueous solution of the $H_2$-antagonist, and subjecting said solution to elevated temperatures sufficient for a period sufficient to cause a reduction in the adverse taste and/or malodor of the $H_2$-antagonist.

12 Claims, No Drawings

PROCESS FOR REDUCING THE ADVERSE TASTE AND MALODOR ASSOCIATED WITH H₂-ANTAGONISTS

FIELD OF THE INVENTION

The present invention is directed to a process for reducing the adverse taste and malodor associated with the $H_2$-receptor antagonists such as nizatidine. The present invention is further directed to such $H_2$-receptor antagonists which exhibit reduced levels of adverse taste and/or malodor.

BACKGROUND OF THE INVENTION $H_2$-receptor antagonists (hereinafter referred to as $H_2$-antagonists) are characterized as a family by their ability to inhibit the secretion of gastric acid. $H_2$-antagonists currently marketed include ranitidine, cimetidine, nizatidine and famotidine. They are currently prescribed for the treatment of duodenal ulcers as well as other hypersecretory states. Prior to FDA approval of these compounds, the mainstay of therapy in the reduction of gastric acidity involved the neutralization of gastric acid with conventional antacids.

One of the chief complaints associated with administration of $H_2$-antagonists is their adverse taste and/or malodor. Many attempts have been made in developing delivery systems which mask the taste/smell of these compounds. These attempts have met with varying degrees of success.

For example, concurrently filed U.S. Ser. No. 08/300,013 discloses a lipid-based liquid composition for suspending therein $H_2$-antagonists. The composition comprises (a) at least one triglyceride or propylene glycol ester of a medium chain length alkanoic acid, wherein at least 95% by weight of the said acid has between 8 and 10 carbon atoms in the chain and at least one acetylated monoglyceride of at least one medium chain length alkanoic acid, having hydroxyl value of 0–15, an acetylation level of at least 95% and a melting point between about 4° and about 12° C., and (b) about 1 to about 5 parts by weight of colloidal silicon dioxide to a total of between about 50 and about 90 parts by weight.

While the above-described liquid composition has application as a liquid dosage form, it does not address the taste/malodor problems which accompany certain $H_2$-antagonists when presented in other dosage forms.

Therefore, it is an object of the present invention to provide a method for reducing the adverse taste and/or malodor of the $H_2$-antagonist itself, thereby allowing all dosage forms of the compound to exhibit reduced levels of adverse taste and/or malodor.

SUMMARY OF THE INVENTION

The present invention is directed to a process for reducing the adverse taste and malodor associated with the $H_2$-antagonists comprising
(a) forming an aqueous solution of an $H_2$-antagonist, and
(b) subjecting said solution to elevated temperatures sufficient for periods sufficient to cause a reduction in the adverse taste and/or malodor of the $H_2$-antagonist.

The present invention is further directed to $H_2$-antagonists which exhibit reduced levels of adverse taste and/or malodor.

DESCRIPTION OF THE INVENTION

The present invention is directed to a process for reducing the adverse taste and malodor associated with $H_2$-antagonists comprising
(a) forming an aqueous solution of $H_2$-antagonist, and
(b) subjecting said solution to elevated temperatures sufficient for a period sufficient to cause a reduction in the adverse taste and/or malodor of the $H_2$-antagonist.

The $H_2$-antagonists useful in the practice of the present invention include cimetidine, nizatidine and famotidine. As exemplified later in the specification, it has been found that the adverse taste and/or malodor of the $H_2$-antagonist ranitidine is not reduced through the practice of the present invention.

The $H_2$-antagonists useful in the practice of the present invention are well known compounds. Dosage forms of these compounds are currently marketed under the trademarks Axid® (nizatidine), Tagamet® (cimetidine) and Pepcid® (famotidine).

The concentration of the $H_2$-antagonists within the aqueous solution is not critical. The process is only truly limited by the solubility of the $H_2$-antagonist. Typically, the $H_2$-antagonist will be present in a concentration of between about 1 wt. % and 2 wt. %, based upon the weight of the final solution. However, this is purely a practical consideration as even highly dilute solutions will benefit from the operation of the present invention.

While not wishing to be limited to the following theory, it is the belief of the Applicants that the adverse taste and malodor associated with $H_2$-antagonists is caused by an impurity entrained within the crystalline structure of the compound. Dissolution or melting of the $H_2$-antagonist allows for the liberation of the impurity from the crystalline structure which may then be removed prior to allowing the recrystallization of the $H_2$-antagonist. In the case of nizatidine, it is believed that the impurity is a nitroethane derivative which, when liberated in aqueous solution, hydrolyzes to dimethanedithiol. It is believed that the dimethanedithiol is the compound responsible for the adverse taste and/or malodor of nizatidine. Upon heating an aqueous nizatidine solution, the dimethanedithiol is volatilized and thereby removed as a possible further contaminant.

Within the practice of the present invention, the temperature to which the aqueous solution of the $H_2$-antagonist is raised is also not narrowly critical. Generally, the temperature must be raised to at least about 80 degrees Centigrade. However, the temperature cannot be elevated to the point where undue degradation of the $H_2$-antagonist occurs. It is preferred to maintain the temperature of the solution below about 120 degrees Centigrade.

In the case of nizatidine, it is preferred that the temperature of the aqueous solution be maintained between 80 and 115 degrees Centigrade. Most preferably, the temperature of the solution is maintained at about 100 degrees Centigrade.

The time period during which the aqueous solution is maintained at the elevated temperature above is also not critical. However, due to the inverse relationship between time and temperature, it is recognized that to achieve a similar reduction in adverse taste and/or malodor, it will be required to maintain the solution at 80 degrees Centigrade for period longer than will be required if the temperature were 100 degrees Centigrade. This having been said, it is preferred that the temperature of the aqueous solution be maintained at an elevated temperature for a period of between 5 minutes and about 2 hours. Periods of more than two hours, while not detrimental to the process, appear to accomplish no further reduction in the malodor and adverse taste. Most preferably, the temperature of the aqueous solution is maintained at an elevated temperature for a period of between 15 minutes and about 1 hour. In the case of nizatidine, maintaining the aqueous solution at a temperature of about 100 degrees Centigrade for about 30 minutes produced product with excellent taste and odor characteristics.

It should further be understood that it is also possible to subject the heated, aqueous solution to varying degrees of vacuum and thereby more readily drive off the volatilized impurities or their byproducts. Use of vacuum will effect, and generally reduce, the temperature to which the solution will have to be elevated and the time for which the solution will have to be maintained at such a temperature.

It has further been noted that the pH of the aqueous solution may be optimized for best operation of the claimed process. In the case of nizatidine, it was found that the best results occurred when the pH was maintained at about 7.8–9.5, most preferably 8.3–8.5.

It should be noted that the reduced adverse taste and/or malodor associated with the $H_2$-antagonist produced in accordance with the present invention may be readily masked, if necessary, with conventional ingredients such as flavors and sweeteners.

The following Examples are offered to illustrate the practice of the present invention. They should not be construed as a limitation on the scope of such invention or its practice.

EXAMPLES

In the following Examples, the following words/phrases are utilized to describe the degree of the odor present before and after the practice of the present invention. These are arranged below in order from most to least offensive.

Very offensive

Offensive

Moderately Offensive

Slightly Offensive

Very Slightly Offensive

Tolerable

Moderately Odious

Slightly Odious

Very Slightly Odious

No Foul Odor.

Example 1

About 7.5 grams of Nizatidine were dissolved with stirring in about 75 ml. of distilled water having a temperature of 72 degrees Centigrade. The solution exhibited a Very Offensive Odor.

The temperature of the solution was then elevated to about 100 degrees Centigrade for 30 minutes. The solution then exhibited a Tolerable odor.

Example 2

About 7.5 grams of Cimetidine HCl were dissolved with stirring in about 75 ml. of distilled water having a temperature of 72 degrees Centigrade. The solution exhibited a Very Slightly Offensive odor.

The temperature of the solution was then elevated to about 100 degrees Centigrade for 30 minutes. The odor then exhibited by the solution was Slightly Odious.

Comparative Example 1

About 7.5 grams of Ranitidine HCl were dissolved with stirring in about 75 ml. of distilled water having a temperature of 72 degrees Centigrade. The solution exhibited a Very Slightly Offensive odor.

The temperature of the solution was then elevated to about 100 degrees Centigrade for 30 minutes. The odor then exhibited by the solution was also Very Slightly Offensive.

Example 3A

About 7.5 grams of Nizatidine were dissolved with stirring in about 75 ml. of distilled water having a temperature of 72 degrees Centigrade. The solution exhibited a Very Offensive odor.

The temperature of the solution was then elevated to about 80 degrees Centigrade for 30 minutes. The solution then exhibited a Moderately Offensive odor.

Example 3B

The procedure of Example 3A was followed except that the solution was maintained at the temperature of 80 degrees Centigrade for 1 hour. The odor then exhibited by the solution was Slightly Offensive.

Example 3C

The procedure of Example 3A was followed except that the solution was maintained at the temperature of 80 degrees Centigrade for 2 hours. The odor then exhibited by the solution was Tolerable.

Example 4A

About 7.5 grams of Nizatidine were dissolved with stirring in about 75 ml. of distilled water having a temperature of 72 degrees Centigrade. The solution exhibited a Very Offensive odor.

The temperature of the solution was then elevated to about 90 degrees Centigrade for 30 minutes. The solution then exhibited a Slightly Offensive odor.

Example 4B

The procedure of Example 4A was followed except that the solution was maintained at the temperature of 90 degrees Centigrade for 1 hour. The odor then exhibited by the solution was Slightly Offensive.

Example 4C

The procedure of Example 4A was followed except that the solution was maintained at the temperature of 90 degrees Centigrade for 2 hours. The odor then exhibited by the solution was Mildly Odious.

Example 5A

About 7.5 grams of Nizatidine were dissolved with stirring in about 75 ml. of distilled water having a temperature of 72 degrees Centigrade. The solution exhibited a Very Offensive odor.

The temperature of the solution was then elevated to about 100 degrees Centigrade for 30 minutes. The solution then exhibited a Tolerable odor.

Example 5B

The procedure of Example 5A was followed except that the solution was maintained at the temperature of 100 degrees Centigrade for 1 hour. The odor then exhibited by the solution was Mildly Odious.

Example 5C

The procedure of Example 5A was followed except that the solution was maintained at the temperature of 100 degrees Centigrade for 2 hours. The odor then exhibited by the solution was Slightly Odious.

We claim:

1. A process for reducing the adverse taste and malodor associated with an $H_2$-antagonist selected from the group consisting of cimetidine, nizatidine and famotidine comprising (a) forming an aqueous solution of the $H_2$-antagonist, and
   (b) subjecting said aqueous solution to elevated temperatures sufficient for a period sufficient to cause a reduction in the adverse taste and/or malodor of the $H_2$-antagonist.

2. The process of claim 1 wherein the aqueous solution is elevated to a temperature ranging from about 80 degrees Centigrade and a temperature below which degradation of the $H_2$-antagonist occurs.

3. The process of claim 1 wherein the aqueous solution is elevated to a temperature ranging from about 80 to about 120 degrees Centigrade.

4. The process of claim 3 wherein the aqueous solution is elevated to a temperature ranging from about 90 to about 110 degrees Centigrade.

5. The process of claim 3 wherein the aqueous solution is elevated to a temperature of about 100 degrees Centigrade.

6. The process of claim 1 wherein the $H_2$-antagonist is nizatidine.

7. The process of claim 6 wherein the aqueous solution is elevated to a temperature ranging from about 80 to about 120 degrees Centigrade.

8. The process of claim 6 wherein the aqueous solution is elevated to a temperature ranging from about 90 to about 110 degrees Centigrade.

9. The process of claim 6 wherein the aqueous solution is elevated to a temperature of about 100 degrees Centigrade.

10. The process of claim 1 wherein the temperature of the aqueous solution is elevated for a period of time of between about 5 minutes and 2 hours.

11. The process of claim 10 wherein the temperature of the aqueous solution is elevated for a period of time of between about 15 minutes and 2 hours.

12. The process of claim 6 wherein the aqueous solution is elevated to a temperature of about 100 degrees. Centigrade for a period of time of about 30 minutes.

* * * * *